(12) United States Patent
Kiso et al.

(10) Patent No.: US 6,852,707 B1
(45) Date of Patent: Feb. 8, 2005

(54) REMEDIES FOR HYPERAMMONEMIA

(75) Inventors: Yoshinobu Kiso, Ibaraki (JP); Taeko Iino, Otsu (JP); Shinzo Kato, Meguro-ku (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/857,695

(22) PCT Filed: Dec. 9, 1999

(86) PCT No.: PCT/JP99/06901

§ 371 (c)(1),
(2), (4) Date: Jun. 8, 2001

(87) PCT Pub. No.: WO00/33850

PCT Pub. Date: Jun. 15, 2000

(30) Foreign Application Priority Data

Dec. 10, 1998 (JP) .......................................... 11-351955

(51) Int. Cl.$^7$ ........................... C12N 5/00; A61K 31/70
(52) U.S. Cl. .............................. 514/53; 514/54; 514/25; 536/4.1; 536/123.1; 536/123.13; 363/21.03; 399/301; 424/93.45; 600/322; 435/253.1
(58) Field of Search .............................. 514/53, 54, 25; 536/4.1, 123.1, 123.13, 25; 363/21.03; 399/301; 424/93.45; 600/32.2; 435/253.1

(56) References Cited

U.S. PATENT DOCUMENTS 5,939,309 A * 8/1999 Suwa et al. ............... 435/253.1

FOREIGN PATENT DOCUMENTS

| EP | 0265970 | | 5/1988 |
| EP | 382355 A2 | | 8/1990 |
| EP | 382355 | * | 8/1990 |
| EP | 0459462 | | 12/1991 |
| JP | 57-4922 A | | 1/1982 |

OTHER PUBLICATIONS

Rikkers, "Portal hemodynamics, intestinal absorption, and postshunt encephalopathy." Surgery, (Aug. 1983), 94(2), 126–133.*

Pai et al., "Treatment of porto-systemic encephalopathy with lactitol versus lactulose: a randomized controlled study." Chung–Hua I Hsueh Tsa Chih (Chinese Medical Journal), (Jan. 1995), 55(1), 31–36.*

Mette Rye Clausen et al., "Lactulose, Disaccharides and Colonic Flora", Drugs, vol. 53 No. 6 (Jun. 1997) pp930–942.

Delzenne N. et al., "Effect of Fermentable Fructo–Oligosac-chardies On Mineral, Nitrogen and Energy Digestive Balance in the Rat", Life Sciences, vol. 57, No. 17 (1995) pp 1579–1587.

Kajihara et al., "Effect of xylooligosaccharides on blood ammonia level" Hepatology, vol. 30, No. 4, part 2, Oct. 1999, p. 292A, XP001057358, Abstract.

Younes et al. "Fermentable Fibres or Oligosaccharides Reduce Urinary Nitrogen Excretion by Increasing Urea Disposal in the Rat Cecum" J. of Nutrition, vol. 125, No. 4 Apr. 1995 pp 1010–1016 XP001063206.

* cited by examiner

Primary Examiner—James O. Wilson
Assistant Examiner—Devesh Khare
(74) Attorney, Agent, or Firm—Paul E. White, Jr.; Manelli Denison & Selter PLLC (57) ABSTRACT

By using xylobiose or xylooligosaccharide containing xylobiose as a main ingredient in place of lactulose, there is provided a blood ammonia lowering agent, a therapeutic agent of hyperammonemia or a therapeutic agent of hepatic encephalopathy that need be adminstered in smaller doses and which have no concern over side effects.

Lactulose conventionally used as such drugs has to be administered in high doses and involves a safety problem when administered to patients with galactosemia or diabetes mellitus. The drug of the invention which contains xylobiose as a main ingredient solves these problems.

6 Claims, 6 Drawing Sheets

(*: with significant difference at p < 0.05; **: with significant difference at p < 0.001)

REMEDIES FOR HYPERAMMONEMIA

This application is the national phase of international application PCT/IP00/05210 filed 3 Aug. 2000 which designated the U.S.

TECHNICAL FIELD

This invention relates to blood ammonia lowering agents as well as therapeutic agents for hyperammonemia or hepatic encephalopathy that are characterized by containing xylobiose as an active ingredient.

BACKGROUND ART

Hyperammonemia and hepatic encephalopathy are generally believed to have the following pathology.

When nitrogenous compounds such as amino acids, amines and purine/pyrimidine bases are metabolized in organs in the living body, ammonia is produced. Besides the ammonia produced in this metabolic process, amino acids produced by digestion and decomposition of dietary protein are also converted to ammonia after absorption into the mucosa of the small intestine and then released into the portal vein. The ammonia generated by *enterobacteria* in the colon is also absorbed. Hence, the intestine plays a major role in the behavior of blood ammonia.

Since ammonia is a toxic substance, every organ has a metabolic mechanism that detoxifies and processes ammonia. In organs other than the liver, two reactions occur, one involving glutamic dehydrogenase to synthesize glutamic acid by incorporating ammonia into (α-ketoglutaric acid and the other for converting the produced glutamic acid to glutamine by binding with ammonia.

In the liver, ammonia is actively processed in the urea cycle. In normal state, ammonia metabolism is strictly regulated and the blood ammonia level is maintained at constant level. However, if some part of the ammonia detoxifying mechanism becomes abnormal or if ammonia detoxification and processing are not fully functional due to hepatic insufficiency or other cause, the blood ammonia increases to cause manifestation of hyperammonemia. If the protein uptake increases, more urea is produced in the liver and so is the urea that is secreted into the upper digestive tract. As a result, the production of ammonia from urea by *enterobacteria* through urease reaction increases to elevate the blood ammonia level.

Hepatic insufficiency is one of the typical diseases that cause hyperammonemia and the encephalopathy that is involved is called hepatic encephalopathy. If the ammonia level in cells increases, α-ketoglutaric acid which is located in the citric acid (TCA) cycle reacts with ammonia to form glutamic acid which further reacts with one molecule of ammonia to become glutamine. This reaction consumes ATP and the decrease in α-ketoglutaric acid impairs the turnover of the TCA cycle; as a result, the net ATP production decreases. The impaired metabolism is noticeable in the brain stem and adversely affects the function of the brain stem reticular formation which is important in the maintenance of consciousness level, thus causing disturbances of consciousness [Akiharu Watanabe, Rinsho Kanfuzengaku (Clinical Study of Hepatic Insufficiency), pp. 26–33, Nagai Shoten, 1994].

With the progress of hepatic insufficiency, the blood urea decreases and ammonia increases. In the urine, urea nitrogen decreases and the proportions of ammoniacal nitrogen, amino nitrogen, etc. in the total urinary nitrogen increase markedly. The liver is an organ having extremely high performance in reserve and its ability to synthesize urea changes little even if 80–90% of it is excised; hence, the increase of blood ammonia is not probably due to the lowering of the urea synthesizing ability; rather, a short circuit between the portal vein and the systemic circulation is formed in consequence of impairment of the hepatic parenchyme and ammonia is directly carried into the systemic circulation via this alternative pass way without passing through the liver [Taira Sakaguchi, Kanshikkan to Tanpakushitsu Taisha, Yakugaku Ryoiki no Byotai Seikagaku (Hepatic Disease and Protein Metabolism — Biochemistry of Pathology in Pharmacy), Hirokawa Shoten, pp. 152–155, 1976].

As hepatic insufficiency worsens, the blood ammonia level increases, whereupon psychoneurotic symptoms appear. In the early period, the patient is declined orientation, attention and concentration and fall into a clouding of consciousness and coma with the progress of the disease. In the later period, tremor and flapping involuntary movements (asterixis) occur in the superior limbs. In EEG, periodic and synchronous characteristic waveform patterns called "three-phase waves" appear [Igaku Daijiten (Encyclopaedia of Medicine), 18 ed., Nanzando, 1998].

The basics of therapy against hyperammonemia lie in suppressing the production of ammonia while promoting the detoxification and processing of ammonia. A most effective way to suppress the production of ammonia is reducing dietary protein uptake and using low-protein diet in the therapy; however, patients with hepatic insufficiency who suffer from decreased serum albumin level due to enhanced decomposition of body protein must take up a minimum maintenance level of protein (1.27 g/kg body weight/day) by all means. However, to patients who are intolerant of protein, even taking up this minimum maintenance level of protein is problematic. It is therefore necessary to develop a method for the treatment of hyperammonemia by other than low-protein diet [Akiharu Watanabe, Rinsho Kanfuzengaku (Clinical Study of Hepatic Insufficiency), pp. 297–307, 1994].

As a method for the treatment of hyperammonemia by other than low-protein diet, administration of lactulose and a nonabsorable antibiotic "neomycin" has heretofore been tried. In 1966, lactulose was first used in the treatment of hepatic encephalopathy (Bircher J. et al. Lancet 1:890–893, 1966) and its effectiveness (80–90%) was later verified by double blind test (Conn HO, et al. Gastroenterol. 72:573–583, 1977). Ever since that time, lactulose has been widely used in both prevention and treatment of hepatic encephalopathy which accompanies fulminant hepatitis and cirrhosis. Lactulose (4-O-β-D-galactopyranosyl-D-fructose) was made from lactose by E. M. Montgomery et al. in 1930 and it is a non-naturally occurring oligosaccharide composed of one molecule each of galactose and fructose. Nonabsorbable antibiotics such as neomycin have side effects (renal disorder and deafness), so the frequency of their use is comparatively low and lactulose has been considered "the drug of first choice" against hyperammonemia [Akiharu Watanabe, Rinsho Kanfuzengaku (Clinical Study of Hepatic Insufficiency), pp. 297–307, 1994].

Lactulose is believed to prevent or ameliorate hyperammonemia and hepatic encephalopathy by the following mechanism of action.

1) Lactulose promotes the growth of organic acid producing *enterobacteria* such as *Bifidobacteria* to lower the pH in the colon, thereby converting the ammonia in the intestine to the ionic form ($NH_4^+$) so as to suppress the absorption of ammonia: 2) Lactulose suppresses the growth of ammonia producing bacteria in the intestine so as to suppress ammonia production in it; 3) When carbohydrates are supplied as a source of energy, *enterobacteria* take up nitrogen compounds (e.g. urea and ammonia) and use them as raw materials for the synthesis of amino acids and proteins so that the ammonia level in the intestine is lowered [Attachment to LACTULOSE MATSU "NIKKEN", Nikken Chemicals Co., Ltd., 1998 and Akiharu Watanabe, Rinsho Kanfuzengaku (Clinical Study of Hepatic Insufficiency), pp. 297–307, 1994].

The human digestive tract has no enzyme that decomposes lactulose into galactose and fructose, so it is held that lactulose is not absorbed into the small intestine but that it reaches the large intestine where it is utilized by *enterobacteria* to exhibit the various functions mentioned above.

In Japan, lactulose is commercially available as powder, syrup, dry syrup and jelly. The powder is usually administered orally daily equivalent dose to 18–40 g lactulose by patients with cirrhosis, it is usually divided in two or three portions and dissolved in cold or lukewarm water prior to use. The syrup should usually be administered as a 65% lactulose solution in a daily dose of 30–60 ml per adult which is divided in three portions.

However, it has been pointed out that lactulose has several defects. For example, lactulose has a lower enterobacterium proliferating effect than other oligosaccharides and must be administered in large amounts in order to obtain the above-described effects. However, lactulose is so sweet that taking it daily in large amounts is considerable pain to the subject. Further, taking large amounts of indigestable saccharides such as lactulose often causes diarrhea, which is another problematic side effect of lactulose.

In addition, lactulose is contraindicated against galactosemic patients (Attachment to LACTULOSE MATSU "NIKKEN", Nikken Chemicals Co., Ltd., 1998). Lactulose preparations contain galactose ($\leq 11\%$) and lactose (s 6%) and cannot be used in patients with galactosemia which is an inborn metabolic abnomaly due to congenital deficiency of the enzyme for the galactose metabolic system. Patients with diabetes mellitus also require meticulous administration of lactulose (Attachment to LACTULOSE MATSU "NIKKEN", Nikken Chemicals Co., Ltd., 1998). The galactose (s 11%) and lactose ($\leq 6\%$) in lactulose preparations are metabolized to glucose, thereby elevating the blood sugar level is problematic for diabetic patients after decomposition and absorption. Care must also be taken when lactulose is used in combination with the antidiabetic drug α-glucosidase inhibitor (Attachment to LACTULOSE MATSU "NIKKEN", Nikken Chemicals Co., Ltd., 1998). The α-glucosidase inhibitor inhibits the decomposition of carbohydrates in food, thereby lowering the absorption of glucose and hence is used in order to suppress the elevation of the blood sugar level after meal. The administration of the α-glucosidase inhibitor is known to induce side effects in the digestive system (e.g. abnormal fermentation with *enterobacteria*); since lactulose also promotes enterobacterial fermentation, using it in combination with the (t-glucosidase inhibitor presents a concern over enhanced side effects.

The following are documented side effects of lactulose from use against hyperammonemia.

Digestive organ: Diarrhea, occasionally accompanied by abdominal pain, borborygmus, bloat, anorexia, vomiting, etc.; if aqueous feces are caused, the administration should be reduced in quantity or suspended [Nihon Iyakuhinshu (Pharmaceuticals in Japan), ed. by Nihon Iryo Joho Center (Japan Medical Information Center), Yakugyojihosha 1997].

As described above, the use of lactulose as a therapeutic of hyperammonemia has been partly replaced by nonabsorbable antibiotics (e.g. neomycin); however, due to the many side effects they cause and since they fail to show the intended effects in many cases of actual use, the nonabsorbable antibiotics are no longer popular today.

Under these circumstances, it has been desired to develop therapeutic agents against hyperammonemia and hepatic encephalopathy that are safe (cause fewer side effects) and easy to take, which develop positive efficacy upon administration in small amounts and which can also be administered to patients with galactosemia and diabetes mellitus.

DISCLOSURE OF THE INVENTION

In order to attain this object, the present inventors performed intensive studies, with particular attention paid to the mechanism of action of lactulose heretofore considered as the drug of first choice, as well as its structure. As a result, they found that when rats feeding on high-protein diet were allowed to drink water having xylobiose or xylooligosaccharide containing xylobiose as a main ingredient dissolved therein, their blood ammonia levels were significantly lowered. When the xylooligosaccharide containing xylobiose as a main ingredient was taken up by patients with cirrhosis who manifested hepatic encephalopathy, neither loose feces nor diarrhea accompanied: the effective dose of the xylooligosaccharide containing xylobiose as a main ingredient was by far smaller than that of lactulose so it could be taken up without any discomfort and the blood ammonia level could be effectively lowered. The present invention has been accomplished on the basis of these findings.

In the first place, the present inventors noted oligosaccharides which are similar to lactulose in having the activity of promoting the growth of organic acid producing *enterobacteria*. Many kinds of such oligosaccharides are known today and include not only the xylooligosaccharide of the invention (constituent monosaccharide; xylose) but also others such as fructooligosaccharide (constituent monosaccharides; glucose and fructose), lactofcurose (constituent monosaccharides; galactose, glucose and fructose), galactooligosaccharide (constituent monosaccharides; galactose and glucose), and isomaltooligosaccharide (constituent mono-saccharide; glucose). It is known that these oligosaccharides differ not only in the type of constituent monosaccharides but also in the mode of binding between monosaccharides and the degree of their polymerization.

These oligosaccharides are known to have the activity of promoting the growth of *enterobacteria* but when they were actually put into culture liquid of various *enterobacteria* and the growth activities of the latter were compared, they were not uniform in growth promoting activity but differed greatly with the type of oligosaccharide [Tomotari Mitsuoka, Bifiduskin no Kenkyu (Study of *Bifidobacteria*), Nippon Bifiduskin Center, Foundation 1994]. In the case of xylooligosaccharide, the growth activity of *Bifidobacteria* commonly called "the good-guy bacteria in the colon" is high and the growth activities of *Bifidobacterium* adolescentis and *B. longum* are particularly high although these activities vary with the degree of polymerization of constituent monosaccharides such as xylose and xylobiose (M. Okazaki et al. *Bifidobacteria* Microflora, 9, 77–86, 1990). It is also known that when oligosaccharides were actually taken by humans, various *enterobacteria* were found in different proportions in the feces depending on the type of oligosaccharide taken up.

It has not been unravelled as to which enterobacterium would be most effective in lowering the blood ammonia level. Further, even with oligosaccharides that are generally known to have the activity of promoting enterobacterial growth, the type of enterobacterium that can be promoted in growth and the expected change in the proportions of *enterobacteria* differ greatly with the type of constituent monosaccharides and the degree of their polymerization (see above) and it is yet to be unravelled as to which oligosaccharide should be chosen to promote the growth of a specified enterobacterium.

It has been suggested that xylooligosaccharide is effective for lowering the blood ammonia level (J. Nutr., vol. 125, pp. 1010–1016, 1995) but this is based on an experiment with mixtures of xylooligosaccharides having different degrees of polymerization and no optimum degree of polymerization of the constituent monosaccharide xylose has been unravelled.

In order to ensure consistent efficacy of pharmaceuticals while reducing their side effects, it is essential that they have the least amount of impurities. In the case of oligosaccharides, all that have different degrees of polymerization of constituent monosaccharides can be impurities, so finding an optimum degree of polymerization is an important element. The present inventors compared the case of using xylobiose on its own with the case of using xylooligosaccharide containing xylobiose as a main ingredient and revealed that xylobiose is the source of activity.

In order to ensure consistent efficacy of pharmaceuticals, stability, in particular stability in vivo, is also an important factor. The stability of oligosaccharides against acids and digestive enzymes is known to vary with the type of oligosaccharides. It has been reported that among the various oligosaccharides known, xylooligosaccharide has high stability in the digestive tract and that xylobiose and xylooligosaccharide can reach the large intestine without being decomposed with gastric acid or digestive enzymes [Masako Okazaki et al. Nihon Eiyo Shokuryo Gakkaishi (Journal of Japanese Society of Nutrition and Food), Vol. 44, No. 1, pp. 41–44, 1991; Masako Okazaki et al. Digestion & Absorption, Vol. 15, No. 2, pp. 19–22, 1992].

Xylobiose and xylooligosaccharide have the further ability to induce the xylan decomposing enzyme from *enterobacteria*, so they are expected to offer the advantage of effective use of dietary xylan and they need be taken in small amounts to ensure positive effects. For example, with respect to the ability of xylooligosaccharide to ameliorate constipation in female adults, a daily uptake of 0.4 g has been reported to be effective [Taeko Iino et al. Nihon Shokumotsu Seni Kenkyukaishi (Journal of Japanese Society of Dietary Fiber), Vol. 1, No. 1, 19–24, 1997]. Therefore, xylooligosaccharide lowers the blood ammonia level and if used as a therapeutic of hyperammonemia and hepatic encephalopathy, it exhibits the efficacy in smaller doses than lactulose and other oligosaccharides, thereby eliminating the major defect of lactulose that it must be administered in so large amounts as to make the patient feel great pain in taking it.

As a further advantage, xylooligosaccharide does not contain galactose at all as a constituent monosacchardide, so it can even be administered to patients with galactosemia against which lactulose is contraindicated. Xylooligosaccharide which will not be metabolized into glucose can be safely administered to patients with diabetes mellitus who require meticulous administration of lactulose and this is another advantage of the xylooligosaccharide.

Xylooligosaccharide is also expected to offer the advantage of lowering the blood ammonia level which would otherwise increase upon exercise, so if it is administered to patients with hepatitis who are on exercise therapy to cure the disease, the exercise can be prolonged enough to enhance the effectiveness of the therapy. As a further advantage, xylooligosaccharide can increase the staying power of long-distance athletes such as marathon runners.

MODES FOR CARRYING OUT THE INVENTION

The xylooligosaccharide used in the invention can be produced by hydrolyzing xylan-containing natural products with xylanase or acid. For example, starting materials such as cottonseed, Japanese parsely, corncob and birch wood are treated with *Trichoderma*-derived xylanase to produce xylooligosaccharide containing at least 30 wt % of xylobiose. Efficient production can be realized by using a substrate-packed reactor consisting of a column packed with xylan-containing natural products. Specifically, xylan is packed in a column and xylanase which selectively adsorbs on xylan is flowed through the column so that it makes continuous contact with the substrate; the enzyme catalyzes hydrolytic reaction to produce xylooligosaccharide containing xylobiose as a main ingredient, which flows out of the column to be purified by passage through an activated charcoal column, ion-exchange chromatography, etc. to produce xylobiose in high efficiency.

The thus obtained xylooligosaccharide was evaluated by the Working Committee of Nihon Kenko Eiyo Shokuhin Kyokai (Japan Health Food and Nutrition Food Association) on Specified Foods for Health on the basis of the approval requirements set forth in Ordinance No. 64 of the Ministry of Health. Labour and Welfare; as a result, it has been held appropriate as an ingredient which, when taken in amounts of 0.7–7.5 g daily, proves effective in improving the gut flora, improving the characteristics of the feces and suppressing harmful intestinal products. The same would apply to the present invention in determining the effective dose of xylooligosaccharide containing xylobiose as a main ingredient; while the appropriate dose depends on symptom, the preferred is 0.7–7.5 g per day. If xylobiose is to be added on its own, the appropriate dose depends on age and symptom and the preferred is 0.2–3 g. If the xylooligosaccharide of the invention is to be used as a pharmaceutical, it can take on various dosage forms including tablet, capsule, powder, microcapsule, dry syrup and enteric nutrient supplement; alternatively, it may be dissolved in water or any other pharmaceutically acceptable carriers to form a syrup. For example, xylooligosaccharide may be mixed with a physiologically acceptable carrier, flavoring agent, vehicle and stabilizer in generally acceptable morphologies. Additives that can be mixed in tablets and the like include binders such as gelatin, vehicles such as crystalline cellulose and lubricants such as magnesium stearate. If the dosage form is a capsule, it may further contain a liquid carrier.

The following examples are provided for the purpose of further illustrating the present invention but are in no way to be taken as limiting.

EXAMPLE 1

Effects of Xylooligosaccharide on Rats Feeding on High-Protein Diet

As is known, when a high-protein diet is taken, the urea level in the blood and cecum increases, eventually elevating the blood ammonia level. The effect of xylooligosaccharide on N excretion from rats feeding on a high-protein diet was investigated and there was made a comparison with lactulose conventionally used in treatment of hepatic encephalopathy.

SD Male rats in a growth stage (20 heads) were fed on a high-protein feed (containing 50% casein) and divided in three groups; the first group consisting of 7 rats were administered xylooligosaccharide (2% aq. sol.) containing 42 wt % xylobiose; the second group also consisting of 7 rats were administered lactulose (2% aq. sol.); the third was a control group consisting of 6 rats which were administered distilled water; the animals were let to drink these liquids ad libitum for 3 weeks. Throughout the test period, there were no effects on the amounts of feed and water taken by the rats and the increase in their body weight. The cumulative uptake was 13.1±0.8 g for xylooligosaccharide and 12.6±0.5 g for lactulose; the daily uptake was 0.62 g for xylooligosaccharide and 0.6 g for lactulose.

For five days that immediately preceded the end of the test, the feces and urine were separately sampled from the individual rats and their N content was measured by the Kjeldahl method. At the end of the test, the rats were biopsied and their blood ammonia level, BUN (blood urea nitrogen) level and intracecal N content were measured.

Figure 1:
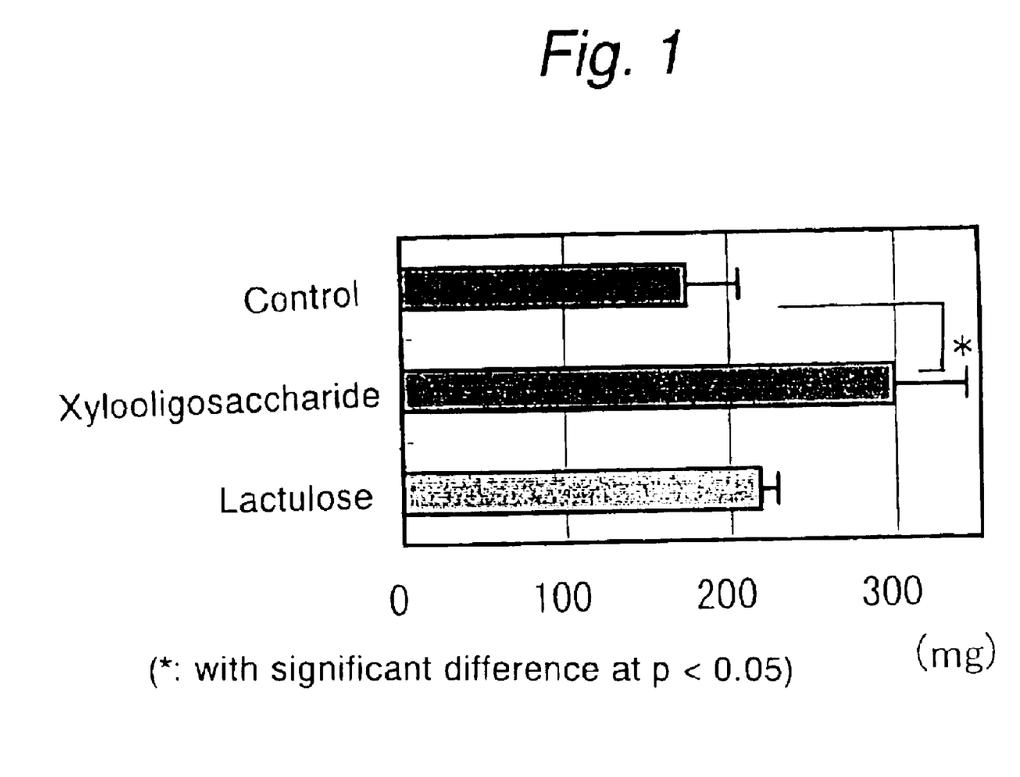
FIG. 1 is a graph showing the effect of administration of xylooligosaccharide or lactulose on the fecal N content of the rats that fed on high-protein diet in Example 1.
Figure 2:
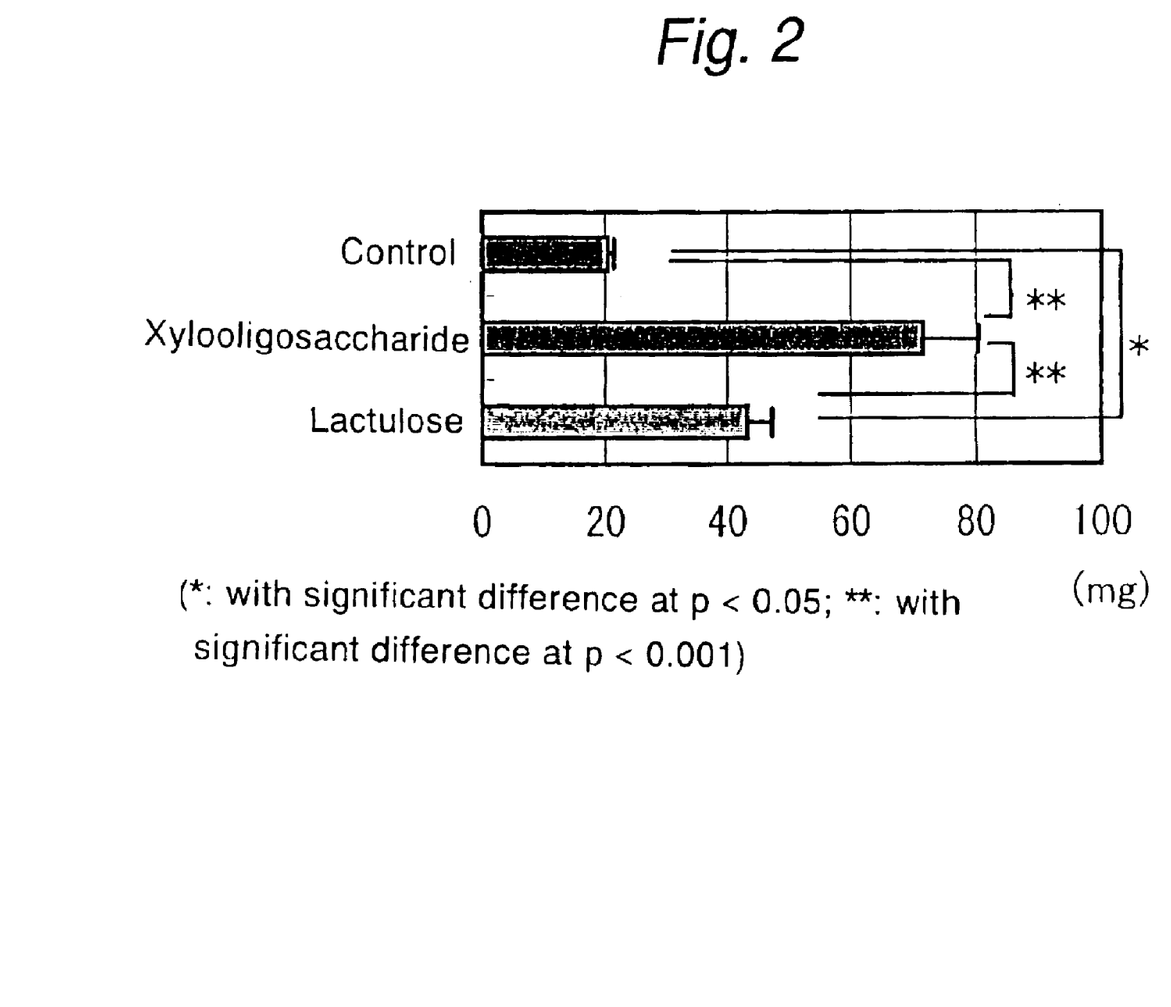
FIG. 2 is a graph showing the effect of administration of xylooligosaccharide or lactulose on the amount of N in the cecal contents of the rats that fed on high-protein diet in Example 1.
Figure 3:
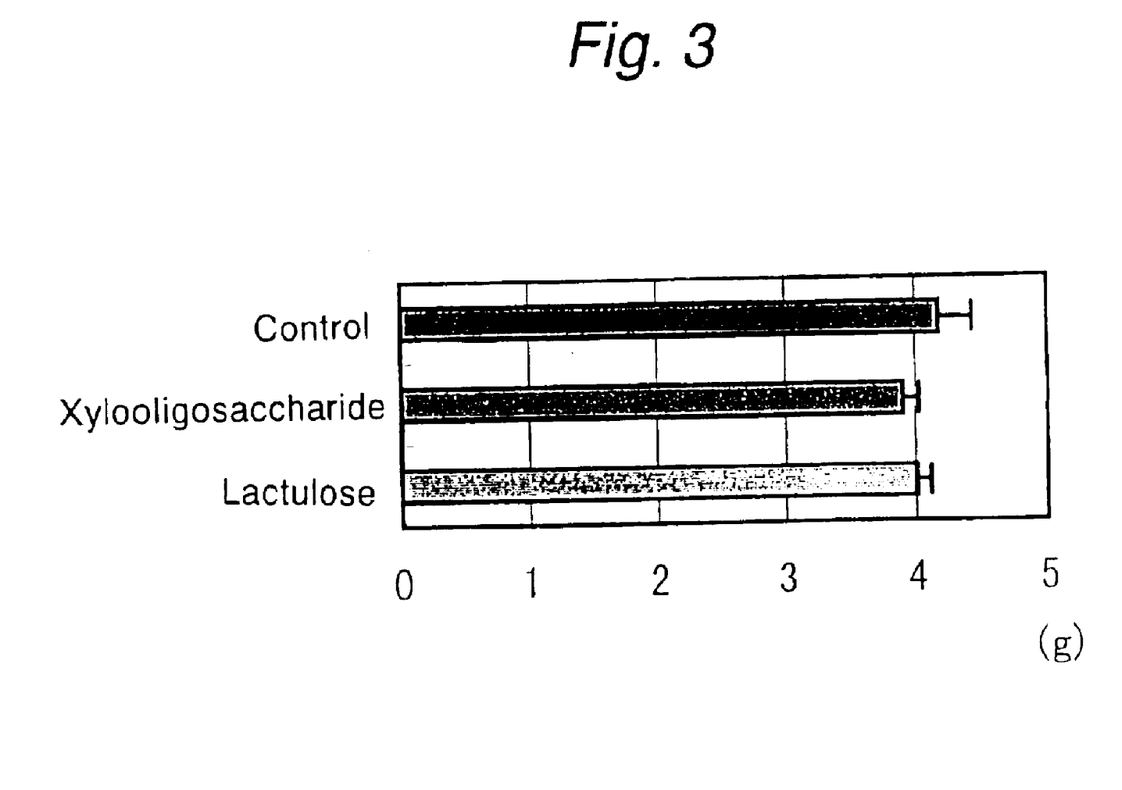
FIG. 3 is a graph showing the effect of administration of xylooligosaccharide or lactulose on the urinary N content of the rats that fed on high-protein diet in Example 1.

In the first group administered xylooligosaccharide, the intracecal N content was about 3.5 times as high as the value for the control group (p<0.001) and the fecal N excretion was almost doubled (p<0.05). In the second group administered lactulose, the intracecal N content was almost doubled (p<0.05) but there was no significant enhancement of fecal N excretion (FIGS. 1 and 2). As for the urinary N excretion, there was little difference among the three groups (FIG. 3).

Figure 4:
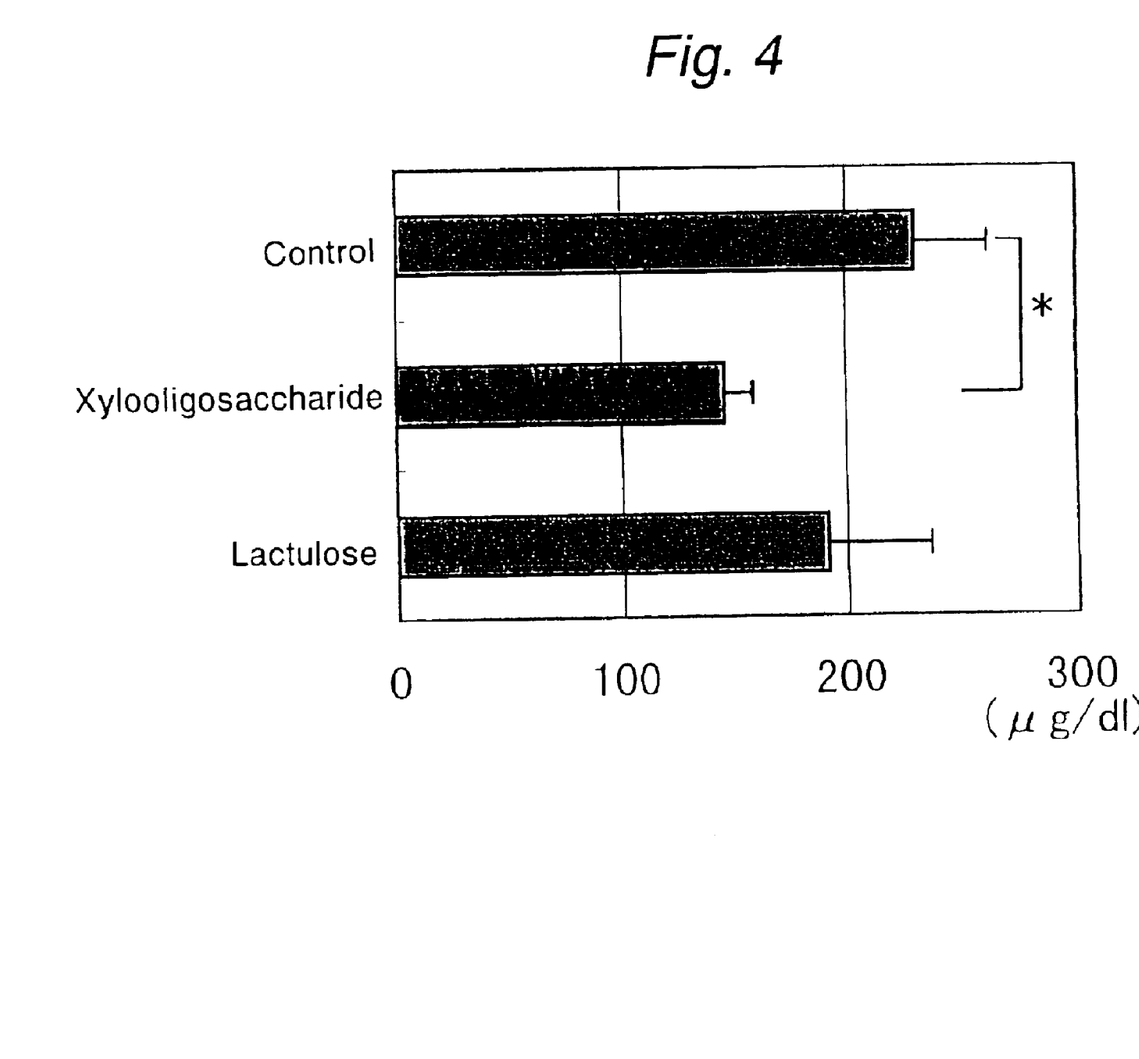
FIG. 4 is a graph showing the effect of administration of xylooligosaccharide or lactulose on the blood ammonia level of the rats that fed on high-protein diet in Example 1.
Figure 5:
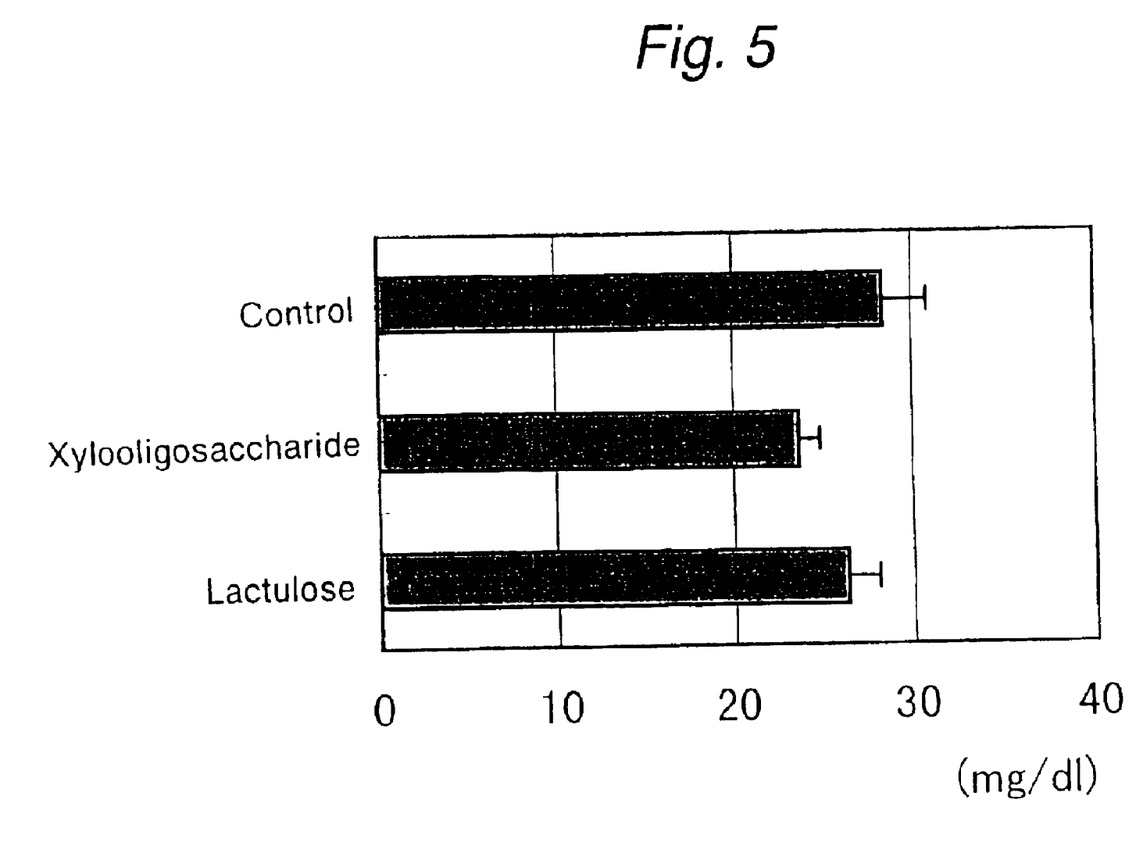
FIG. 5 is a graph showing the effect of administration of xylooligosaccharide or lactulose on the blood urea nitrogen (BUN) of the rats that fed on high-protein diet in Example 1.

The blood ammonia level in the first group administered xylooligosaccharide was significantly lower than the value for the control group (p<0.05) and the BUN level tended to decrease, not significantly though (FIGS. 4 and 5). In the second group administered lactulose, there was found no distinct effect on any of the parameters.

From these results, it was clear that the xylooligosaccharide effectively lowered the blood ammonia level, whereby the amount of the feces was increased accordingly to enhance the fecal N excretion. Lactulose did increase the intrafecal N content but not so much as to lower the blood ammonia level.

EXAMPLE 2

Effects of Xylobiose on Rats Feeding on High-Protein Diet

SD Male rats in a growth stage (15 heads) were fed on a high-protein feed (containing 50% casein) and divided in three groups; the first group consisting of 5 rats were administered 0.5% xylobiose; the second group also consisting of 5 rats were administered 1.0% xylobiose; the third was a control group consisting of 5 rats which were administered distilled water; the animals were let to drink these liquids ad libitum for 3 weeks. Throughout the test period, there were no effects on the amounts of feed and water taken by the rats and the increase in their body weight. The cumulative uptake was 4.7±0.2 g for 0.5% xylobiose and 7.5±0.6 g for 1.0% xylobiose; the daily uptake by the two groups was 0.24 g and 0.37 g, respectively.

At the end of the test, blood was sampled from the rats and the blood ammonia level was measured.

Figure 6:
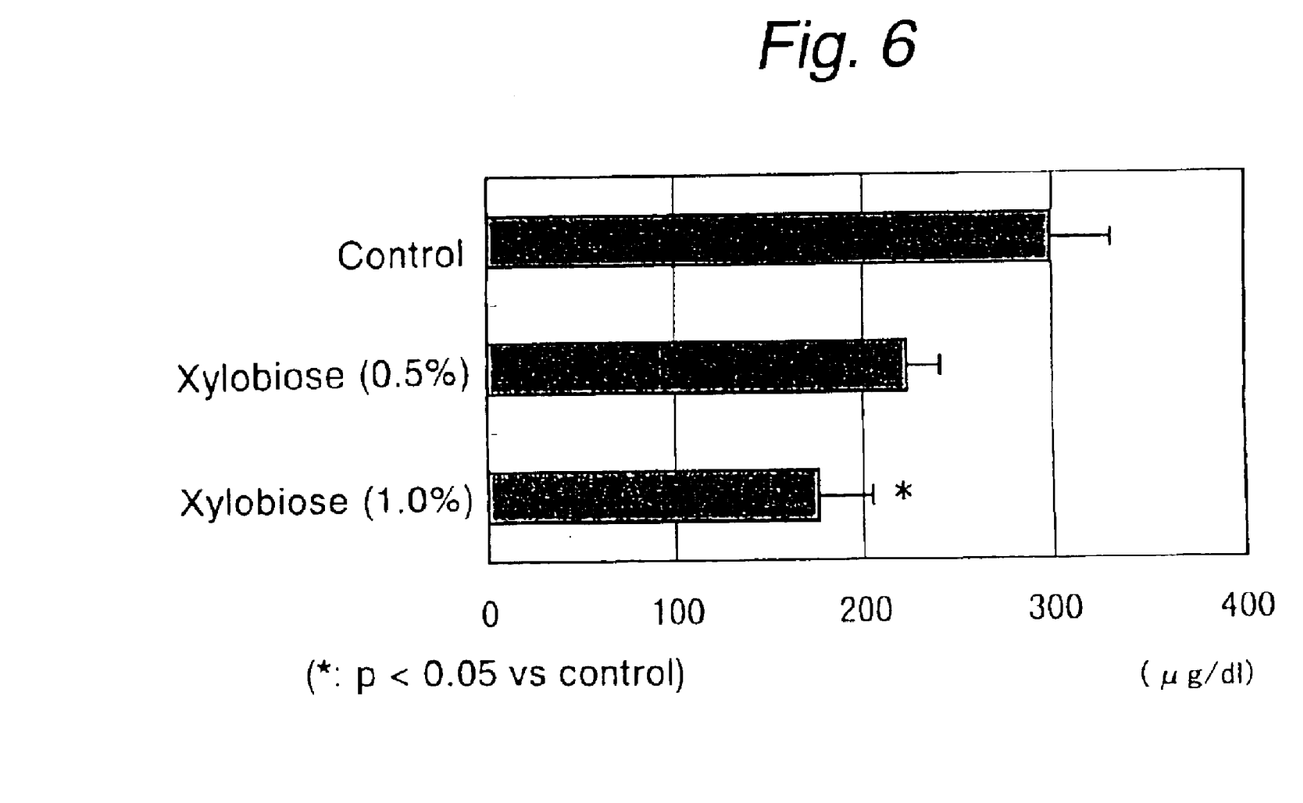
FIG. 6 is a graph showing the effect of administration of xylobiose on the blood ammonia level of the rats that fed on high-protein diet in Example 2.

As FIG. 6 shows, the blood ammonia level in the rats administered xylobiose was lower than the value for the control group at each of the concentrations tested and it was significantly low in the group administered 1.0% xylobiose (p<0.05).

The xylooligosaccharide used in Example 1 contained about 42 wt % of xylobiose. Therefore, the first group in Example 1 which was administered 2% xylooligosaccharide took up almost the same amount of xylobiose as the group in Example 2 which was administered 1% xylobiose. Since the efficacy was comparable in the two groups, xylobiose was verified to be the active ingredient in xylooligosaccharide.

EXAMPLE 3

Effect of Xylooligosaccharide on Patients with Hepatic Encephalopathy (i)

Patients with cirrhosis who did not involve overt encephalopathy and who showed sub-high blood ammonia levels were asked to take 3 g of xylooligosaccharide daily for 4–8 weeks. The sacchardie composition was as follows on a weight basis: about 34% of xylobiose: about 39% of xylotriose or higher oligomer; about 26% of xylose; and about 1% of others. Two weeks later, the blood ammonia level was measured. In the five cases of cirrhosis, the blood ammonia level dropped significantly as the result of administering xylooligosaccharide (initial value: 90.8±29.2 $\mu$mol/L; after 2 wk of administration: 45.0±13.3 mmol/L). There were observed no particular side effects of xylooligosaccharide.

EXAMPLE 4

Effect of Xylooligosaccharide on Patients with Hepatic Encephalopathy (2)

Patients with hepatic encephalopathy were administered daily 3 g of xylooligosaccharide (the same as in Example 3) for two weeks. One week after the start of administration, the blood ammonia level began to decrease. The administration was then suspended and one week later, the blood ammonia level was found to rise. When administration of xylooligosaccharide was resumed, the blood ammonia level droped again.

Since the required dose of xylooligosaccharide was only 3 g/day, no patient complained of pain during administration. There were also no side effects including diarrhea and loose feces.

EXAMPLE 5

Effect of Xylooligosaccharide on Patients with Hepatic Encephalopathy (3)

In patients with hepatic encephalopathy receiving prolonged treatment with lactulose in a daily dose of 75 ml (60% lactulose solution), lactulose had failed to suppress the increase in blood ammonia level. When the treatment was combined with administration of xylooligosaccharide (the same as in Example 3) in a daily dose of 3 g, the blood ammonia level began to decrease. Then the administration of lactulose was suspended and xylooligosaccharide alone was administered; the blood ammonia level still remained low.

Since the required dose of xylooligosaccharide was only 3 g/day, no patient complained of pain during administration. There were also no side effects including diarrhea and loose feces.

Thus, in both animal and human experiments, xylobiose and xylooligosaccharide containing xylobiose as a main ingredient proved to have the ability to lower the blood ammonia level and no pain was felt during administration of these compounds, nor did occur diarrhea. It can therefore be concluded that xylobiose and xylooligosaccharide containing xylobiose as a main ingredient are particularly effective in ameliorating the symptoms of patients with hyperammonemia and hepatic encephalopathy.

INDUSTRIAL APPLICABILITY

The prior art has had no effective means by which the increase in blood ammonia level that accompanies hyperammonemia and hepatic encephalopathy can be suppressed without patients feeling pain or discomfort. However, if xylobiose or xylooligosaccharide containing xylobiose as a main ingredient is administered according to the invention, the blood ammonia level can be effectively lowered without causing pain or discomfort during administration, thereby ameliorating the symptoms of hyperammonemia and hepatic encephalopathy.

What is claimed is:

1. A blood ammonia lowering agent containing xylooligosaccharide containing at least 30 wt % to less than 45 wt % of xylobiose, as an active ingredient.

2. The blood ammonia lowering agent according to claim 1, which comprises said xylobiose or said xylooligosaccharide and a pharmaceutically acceptable carrier.

3. A therapeutic agent of hyperammonemia containing xylooligosaccharide containing at least 30 wt % to less than 45 wt % of xylobiose, as an active ingredient.

4. The therapeutic agent of hyperammonemia according to claim 3, which comprises said xylobiose or said xylooligosaccharide and a pharmaceutically acceptable carrier, wherein said therapeutic agent has the activity of promoting the growth of organic acid producing *enterobacteria*.

5. A therapeutic agent of hepatic encephalopathy containing xylooligosaccharide containing at least 30 wt % to less than 45 wt % of xylobiose, as an active ingredient, wherein said therapeutic agent has the activity of promoting the growth of organic acid producing *enterobacteria*.

6. The therapeutic agent of hepatic encephalopathy according to claim 5, which comprises said xylobiose or said xylooligosaccharide and a pharmaceutically acceptable carrier.

* * * * *